US009981264B2

(12) United States Patent
Greef et al.

(10) Patent No.: US 9,981,264 B2
(45) Date of Patent: May 29, 2018

(54) NITROCELLULOSE EXTRUSION FOR POROUS FILM STRIPS

(71) Applicant: Grace Bio-Labs, Inc., Bend, OR (US)

(72) Inventors: Charles Greef, Bend, OR (US); Joshua Snider, Bend, OR (US); Steven Weaver, Bend, OR (US); Jennipher Grudzien, Bend, OR (US)

(73) Assignee: Grace Bio-Labs, Inc., Bend, OR (US)

( * ) Notice: Subject to any disclaimer, the term of this patent is extended or adjusted under 35 U.S.C. 154(b) by 134 days.

(21) Appl. No.: 14/931,512

(22) Filed: Nov. 3, 2015

(65) Prior Publication Data

US 2016/0121323 A1 May 5, 2016

Related U.S. Application Data

(60) Provisional application No. 62/075,126, filed on Nov. 4, 2014.

(51) Int. Cl.

*G01N 21/75* (2006.01)
*B01L 3/00* (2006.01)
*G01N 33/558* (2006.01)
*B05B 3/18* (2006.01)

(52) U.S. Cl.

CPC .......... *B01L 3/5023* (2013.01); *G01N 33/558* (2013.01); *B01L 2200/025* (2013.01); *B01L 2200/12* (2013.01); *B01L 2300/0825* (2013.01); *B05B 3/18* (2013.01)

(58) Field of Classification Search

CPC ............. B01L 3/5023; B01L 2200/025; B01L 2300/0825; B01L 2200/12; G01N 33/558; B05B 3/18

See application file for complete search history.

(56) References Cited

U.S. PATENT DOCUMENTS

| | | | |
|---|---|---|---|
| 3,900,629 A | 8/1975 | Spencer | |
| 4,956,302 A | 9/1990 | Gordon et al. | |
| 5,527,673 A | 6/1996 | Reinhartz et al. | |
| 5,766,961 A | 6/1998 | Pawlak et al. | |
| 5,798,273 A | 8/1998 | Shuler et al. | |
| 6,214,629 B1 | 4/2001 | Freitag et al. | |
| 6,472,226 B1 | 10/2002 | Barradine et al. | |
| 6,607,922 B2 | 8/2003 | LaBorde | |
| 6,824,975 B2 | 11/2004 | Hubscher et al. | |
| 2009/0305907 A1 * | 12/2009 | Webster ................ | B01L 3/0262 506/23 |

FOREIGN PATENT DOCUMENTS

| | | | |
|---|---|---|---|
| WO | 008466 A2 | 2/2000 | |

* cited by examiner

*Primary Examiner* — Dennis White
(74) *Attorney, Agent, or Firm* — McCoy Russell LLP

(57) ABSTRACT

Methods and systems are provided for a lateral flow test device. In one example a lateral flow test device may include a housing comprising an upper first portion and a lower second portion, the lower second portion further including a planar surface, a nitrocellulose matrix strip, the strip disposed on the planar surface, and one or more ligand regions included in the strip, the ligand regions comprising one or more ligands. The strip may be formed from a liquid polymer mixture dispensed onto the planar surface via a dispensing device positioned vertically above the planar surface.

9 Claims, 6 Drawing Sheets

NITROCELLULOSE EXTRUSION FOR POROUS FILM STRIPS

CROSS REFERENCE TO RELATED APPLICATION

The present application claims priority to U.S. Provisional Patent Application No. 62/075,126, entitled "NITROCELLULOSE EXTRUSION FOR POROUS FILM STRIPS," filed on Nov. 4, 2014, the entire contents of which are hereby incorporated by reference for all purposes.

FIELD

The present application generally relates to methods and systems for nitrocellulose polymer films and, in one example, to methods and systems for directly casting nitrocellulose film strips.

BACKGROUND AND SUMMARY

Lateral flow assays (LFA) use a porous polymeric film, usually comprising nitrocellulose (cellulose nitrate) on a carrier plastic, to provide a wicking medium to transfer liquid that contains assay components from an origin through a region of immobilized ligands, wherein interaction of binding pairs and detection of bound ligand pairs can occur.

LFAs are commonly used as diagnostic test devices to detect the presence of biological molecules by a capillary action mechanism of flowing biomolecule solutions through a porous strip. As the sample passes through the strip's pores and regions containing a biomolecular ligand specific to an analyte of interest, any molecules of the analyte of interest, if present, will be bound and immobilized by the previously affixed biomolecular capture ligand. Labeling methods that allow visualization of the bound biomolecule complex can then provide determination of the presence or absence of the biomolecule of interest. In this way, a sample of unknown composition may be applied to the origin, and capillary action (wicking) moves the liquid through the length of the film strip.

One example LFA test is the human pregnancy test. Other common applications are related to the detection of toxic compounds, infectious diseases, allergens, chemical contaminants and illicit drugs, etc. LFA tests are particularly useful in the area of point-of-care testing, which eliminates the need of time-consuming laboratory work so that test results can be detected visually within a relatively short time frame, such as in 5-30 minutes. LFA tests are also used in academic and research settings to detect specific proteins of biomedical and chemical interest.

Methods to make such lateral flow assays devices as described above are described in WO00/08466 by Freitag et al. (U.S. Pat. No. 6,214,629 B1). Described therein is a diagnostic device that incorporates both a dry porous carrier in the form of a nitrocellulose sheet, and a housing for that carrier that incorporates a sample inlet.

However, the inventors herein have recognized potential issues with such systems. As one example, the LFA devices by Freitag et al. and others are cumbersome and labor intensive to produce because of the cutting and assembly steps required to fabricate the final device. LFA devices are typically constructed in a multi-step process in which the nitrocellulose film is cast to a large sheet, functionalized with immobilized capture ligands, blocked against further protein binding, cut into strips, and assembled into a single use device. The process is time consuming, and contributes a large fraction of the production cost as well as the introduction of variability.

In one example, the issues described above may be addressed by a lateral flow assay device, wherein the device is made by casting a polymer mixture containing nitrocellulose directly to a substrate or device housing. This direct casting method thus eliminates multiple processing and assembly steps. In another aspect, one or more combinations and formulations of the components of a polymer mixture, including, but not limited to a solvent, non-solvent, and nitrocellulose, as well as the conditions under which the mixture is allowed to polymerize and dry, may be regulated and altered to achieve a desired pore size and uniformity of a porous nitrocellulose strip. For example, the relative humidity and/or the temperature of the environment in which the nitrocellulose strip is cast and cured may be adjusted to regulate the rate at which volatile components of a polymer mixture evaporate. By adjusting the rate at which the volatile components evaporate, the resulting pore size of the nitrocellulose strip may be adjusted to a desired pore size. In this way, the resulting strip has wicking and biomolecular binding properties that allow development of desired lateral flow biomolecular detection assays.

In another example, a device may comprise a housing comprising an upper first portion and a lower second portion, the lower second portion further including a planar surface, a nitrocellulose matrix strip, the strip disposed on the planar surface, and one or more ligand regions included in the strip, the ligand regions comprising one or more ligands. In this way, separate sheets of nitrocellulose may be avoided, and thus improved manufacturing may be achieved. The strip may be of various forms, including linear, curved, S-shaped, sinuous, and/or angled.

In yet further examples, a method may comprise positioning a dispensing device a threshold vertical distance above a substrate, dispensing a liquid polymer mixture from the dispensing device onto a planar surface of the substrate, and while dispensing the polymer mixture, moving the dispensing from a first position to a second position. Further, the method may comprise, in response to the dispensing device reaching the second position, terminating the dispensing, and drying the mixture.

Another aspect includes a method for producing a nitrocellulose strip on a substrate by using a dispensing device; providing a removable framed mask on top of the substrate to define the shape, size and thickness of the strip; dispensing a nitrocellulose-based polymer mixture through the frame onto the substrate; and spreading the dispensed mixture with the dispensing head in a programmed fashion.

An advantage is the ability to produce nitrocellulose-based strips for LFA comprising a plurality of pores of a uniform size due to controlled evaporation of the components of the polymer mixture without the need for inefficient processing and assembly steps. This enables an automatable fabrication process that will result in more reproducible products than those currently available with multi-component devices assembled in a multi-step process.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

Figure 1:
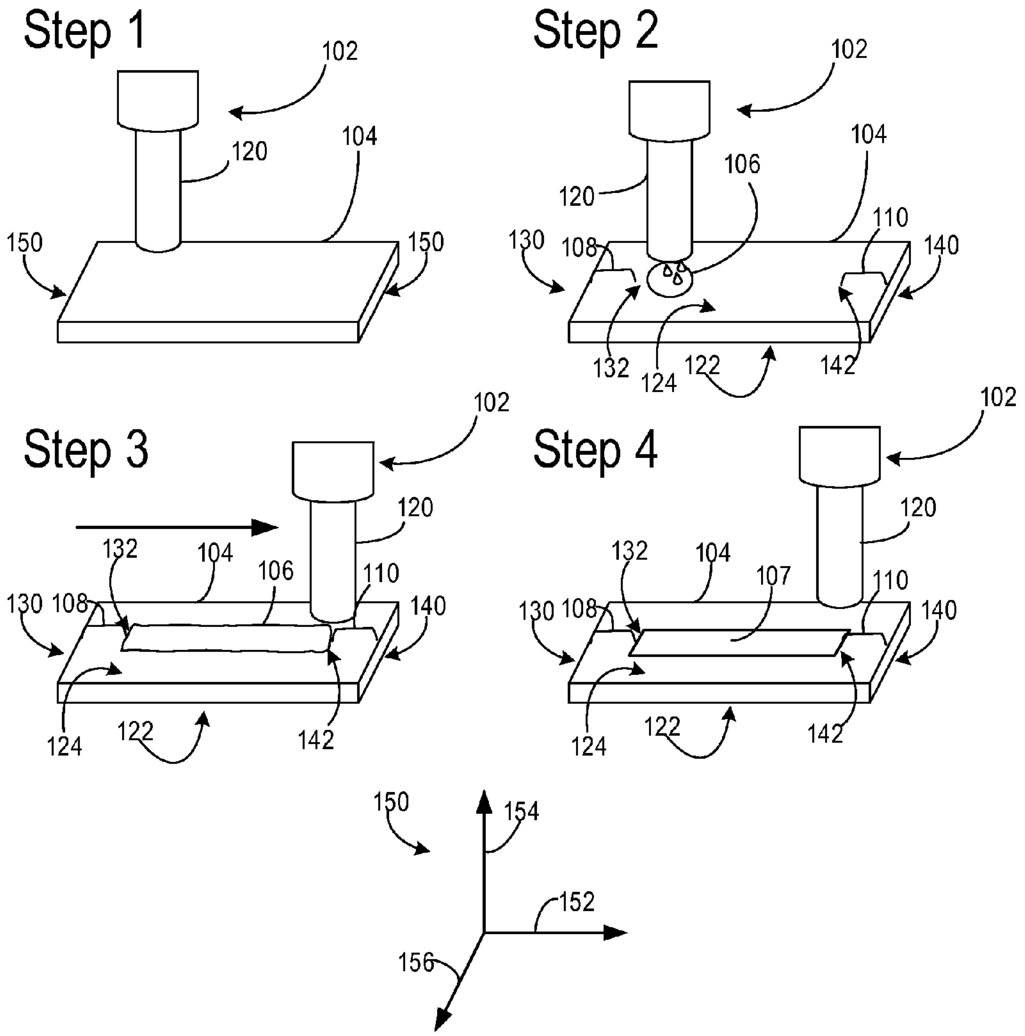
FIG. 1 is a schematic depicting a lateral flow assay device and steps associated with production of an individual lateral flow assay strip.

Note that the drawings are not to scale, and that as such, other relative dimensions may be used. Further, the drawings may depict components directly or indirectly touching one another and in contact with one another and/or adjacent to one another, although such positional relationships may be modified, if desired. Further, the drawings may show components spaced away from one another without intervening components therebetween, although such relationships again could be modified, if desired.

DETAILED DESCRIPTION

The present application relates to a lateral flow test device comprising a porous nitrocellulose-based strip and a method of producing the aforementioned strip by utilizing a dispensing device programmed to spread a polymer mixture into a pre-defined shape. The polymer mixture includes at a minimum a combination of a solvent, a non-solvent, and nitrocellulose. Upon drying, the polymer mixture becomes a nitrocellulose-based strip. In one embodiment, the solvent may dissolve the nitrocellulose, while the non-solvent may be miscible with the solvent at a given concentration, but may phase separate when the non-solvent concentration exceeds a certain threshold.

In addition, the application provides various formulations of a polymer mixture, wherein the polymer mixture may comprise variable proportions of one or more solvents, meta-solvents, non-solvents, and/or nitrocellulose, additives, etc. Furthermore, conditions under which the polymer mixture may dry to yield desired characteristics, such as a particular pore size, are provided. Capillary flow of liquid through a nitrocellulose film is, in part, dependent on the pore size of the polymer film; therefore by controlling the pore size of the polymer film, one can control the flow rate of liquid through the film. Achieving a desired pore size may also enable maximal detection of a particular protein in a given assay, and is contingent on a selected combination of solvent, non-solvent, and nitrocellulose, as well as on one or more conditions under which one or more of these components may dry and polymerize. More specifically, one determinant of pore size formation is the differential evaporation rates of each component (e.g., the solvent and non-solvent). To control the evaporation rates of a polymer mixture, various incubation environments, such as temperature and solvent vapor concentration, may be modulated. Therefore, control over such conditions may allow optimization of a desired pore size and uniformity, and ultimately the performance characteristics of the films.

Additionally, the method disclosed herein may comprise a casting of the polymer mixture directly to a substrate and/or housing by a robotic dispensing device, and thus eliminates multiple processing and assembly steps. Thus, manufacturing of LFA devices using hand-cutting of individual strip and installation of each strip onto a substrate housing may be reduced. In this way, it may be possible to improve manufacturing efficiency by depositing nitrocellulose film directly into or onto an assay device so that film strip cutting, functionalization, and assembly steps are reduced.

Figure 2:
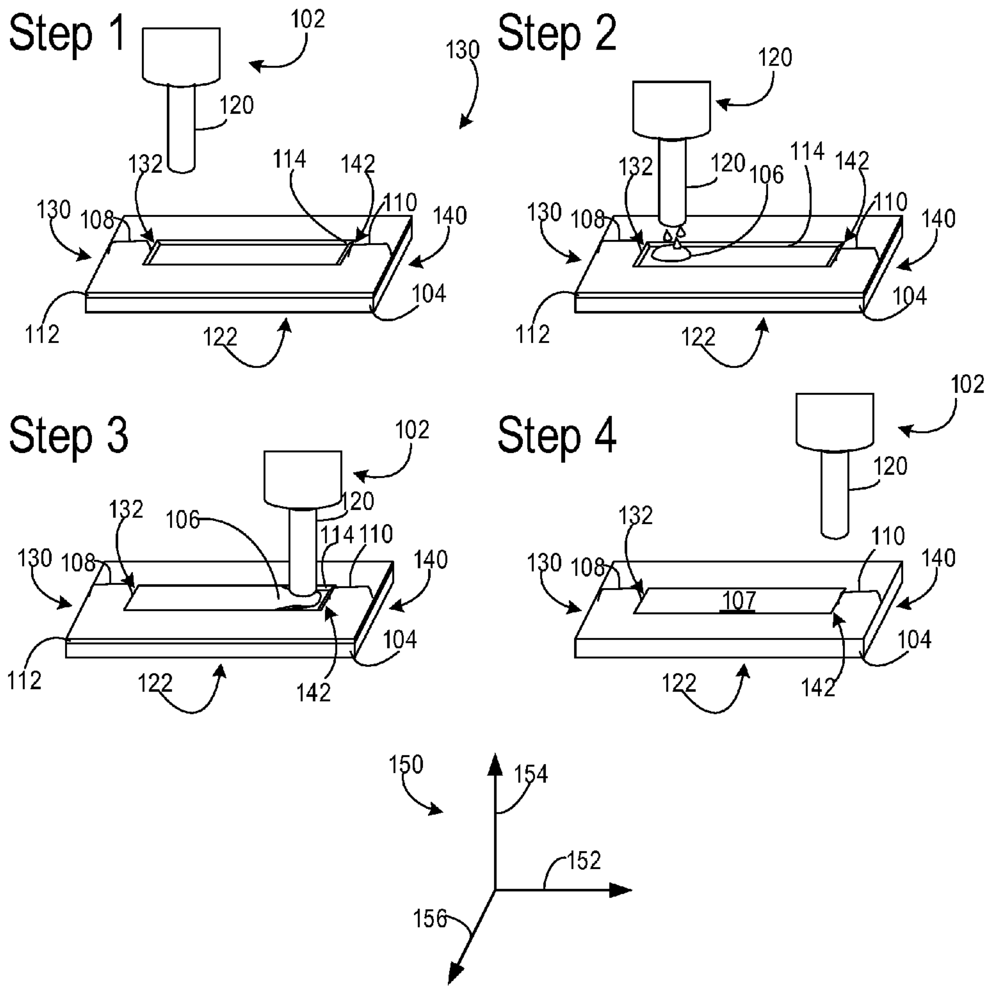
FIG. 2 is a schematic depicting another embodiment of the lateral flow assay device of FIG. 1, including a mask, and steps associated with production of an individual lateral flow assay strip.
Figure 3:
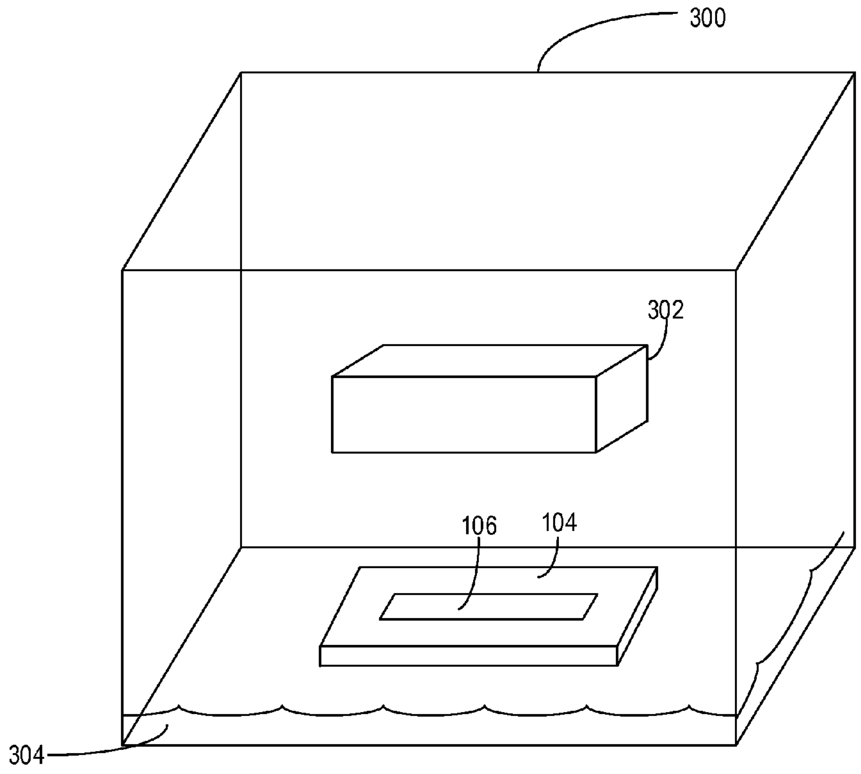
FIG. 3 is a schematic depicting the lateral flow assay strip of FIGS. 1 and 2, disposed within a chamber.
Figure 4:
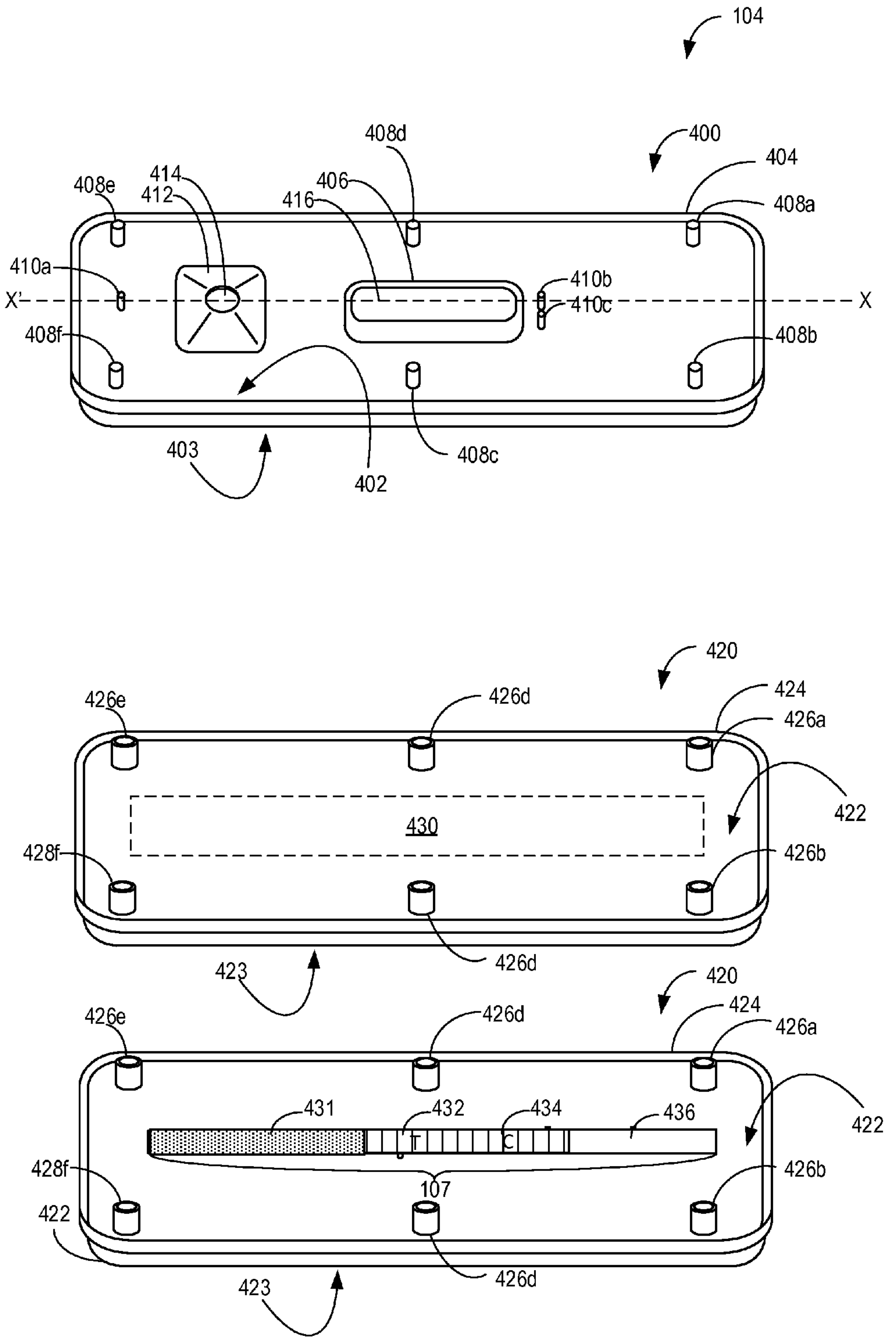
FIG. 4 is an enlarged view of an example of a substrate and housing.
Figure 5:
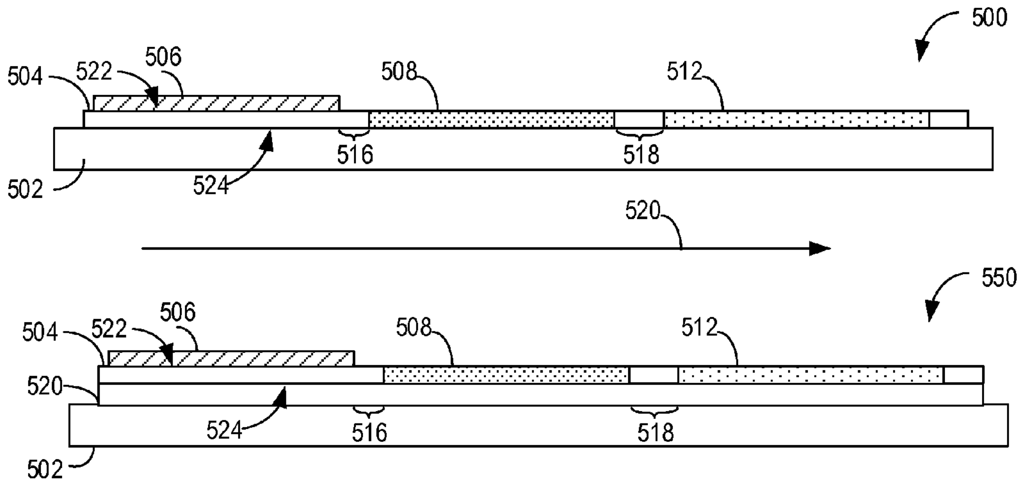
FIG. 5 is an enlarged view of examples of a lateral flow assay strip.
Figure 6:
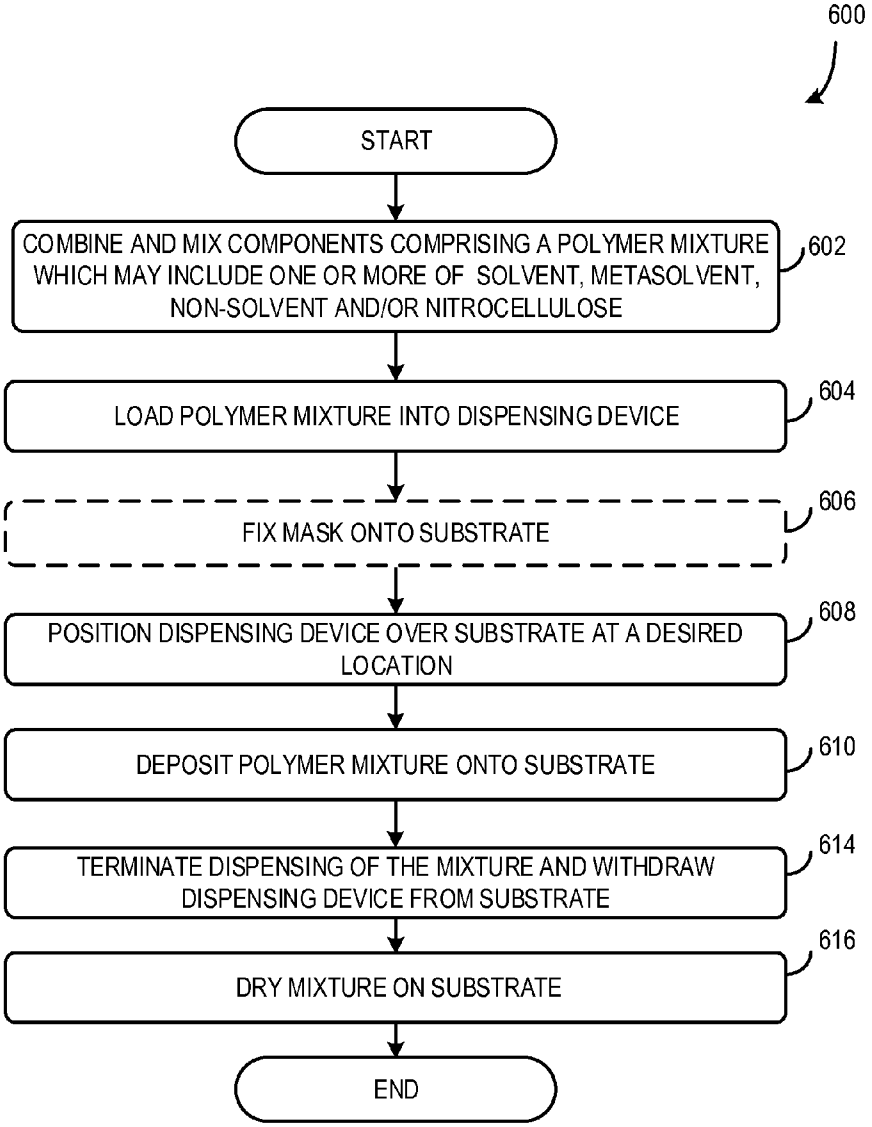
FIG. 6 is an example method for production of a lateral flow assay strip.

FIG. 1 shows an example device for depositing of a polymer mixture in order to form a nitrocellulose-based strip. FIG. 2 shows a system similar to that shown in FIG. 1, but with an additional framed mask forming a well to produce a specific shape of a polymer mixture. FIG. 3 shows an example of a polymer mixture strip drying in a controlled chamber. FIG. 4 shows an enlarged view of an example of a substrate that may be included in the device of FIG. 1. Further, FIG. 5, shows an example of a lateral flow assay strip that may be produced via the device of FIG. 1. FIG. 6 shows a flow chart of an example method for production of a lateral flow assay strip.

FIGS. 1 and 2 show a dispensing device 102 for dispensing a polymer mixture 106 onto a substrate 104 to form a porous polymer strip 107 or lateral flow assay (LFA) strip 107 when dried. Specifically, FIGS. 1 and 2 show four sequential steps in the dispensing of the mixture 106 onto the substrate 104: step 1, followed by step 2, followed by step 3, and followed by step 4. Each of the steps will be described in greater detail below with reference to the description of FIGS. 1 and 2. In some examples, substrate 104 may be referred to as housing 104.

FIG. 2, shows an example where a mask 112 is positioned on top of the substrate, the mask 112 including a well 114, into which the polymer mixture 106 be dispensed. The mask 112 may also be referred to herein as cover 112. Thus, the well 114 may be a recess within the mask 112 that contains the mixture 106 to within the interior of the volume it defines. As such, the shape and size of the porous polymer strip 107 may be more controlled, and may be defined by the well 114. The polymer strip 107 may therefore be sized to approximately the same size as the well 114. Said another way, the strip 107 may be fully contained within the mask 112. In this way, the uniformity of the shape and size of the polymer strip 107 from strip to strip may be increased, and variance in the shape and size of the polymer strip 107 may be reduced. Since the dispensing device 102 and substrate 104 are the same in FIGS. 1 and 2, components of the dispensing device 102 and substrate 104 introduced in FIG. 1 may not be reintroduced or discussed again in the description of FIG. 2.

In some examples, the liquid polymer mixture 106 is a mixture of nitrocellulose, solvent, and non-solvent. Thus, in the description herein, the liquid polymer mixture 106 may be referred to as liquid nitrocellulose matrix 106. In one embodiment, the solvent may dissolve the nitrocellulose, while the non-solvent may be miscible with the solvent at a given concentration, but may phase separate when the evaporation of the solvent causes the relative non-solvent concentration to exceed a certain threshold. Specifically, in one example, the liquid polymer mixture 106 comprises a higher relative solvent concentration such that the non-solvent and solvent are completely miscible and allow dissolution of nitrocellulose by said solvent. In addition, the solvent may be more volatile than the non-solvent, so that after a selected amount of time under controlled conditions, the solvent concentration decreases in the mixture due to differential evaporation. As the relative concentration of non-solvent increases beyond a critical threshold, a phase separation occurs, causing droplets of non-solvent to form within the solvent/nitrocellulose solution in the form of an emulsion. The evaporation of solvent also increases the nitrocellulose polymer concentration beyond a critical solubility threshold, at which point the mixture solidifies from the remaining solvent solution, causing emulsified non-solvent droplets within the solvent to form voids amongst the polymerized nitrocellulose. The droplets are the structural bases for the pores within the solidified nitrocellulose. In other words, the formation of pores as the polymer mixture dries is dependent on the differential evaporation rates of the solvent and non-solvent. Since the droplets of emulsified non-solvent will not contain any nitrocellulose, their size and distribution in the emulsion defines the size, shape, and distribution of the eventual pores in the film after all liquids may be removed.

In some embodiments, the solvent for the nitrocellulose mixture includes one or more of acetone, methyl acetate, tetrahydrofuran, toluene, and propylene oxide. In other embodiments, the solvent may include another appropriate solvent. Appropriate non-solvents that are miscible with said solvents at certain relative concentrations but phase separate when the relative non-solvent concentration exceeds a critical threshold include, but are not limited to, water, butanol, ethanol, and isopropanol, and mixtures of these non-solvents. Unlike the solvents, the non-solvents do not cause solvation of the nitrocellulose.

In yet another embodiment, other components included in the polymer mixture of the device disclosed herein may comprise detergents, hydrophilic additives, plasticizers, and/or meta-solvents. According to the current disclosure, meta-solvents are liquids in which nitrocellulose is not soluble in a pure solution, but when combined with a solvent will allow for nitrocellulose solvation. For example, ethanol is not a solvent of nitrocellulose in pure form, but mixtures of ethanol and acetone are nitrocellulose solvents; therefore in combination with acetone, ethanol is considered a meta-solvent. Use of meta-solvents can alter the overall evaporation rate of solvent, allowing manipulation and control over the rate of relative solvent/non-solvent concentration changes, and thus the polymer film pore size.

In one embodiment, one of a grade or type of nitrocellulose may be varied such that physical and chemical features of the resulting nitrocellulose-based strip may be optimized. Generally, nitrocellulose is graded according to its solution viscosity under certain sets of conditions. Viscosity is related to polymer chain length, in which larger chain lengths afford a higher viscosity solution in standard conditions, which is described by the designation of time for a weight to travel a set distance through the solution (in seconds). In one embodiment, grades of nitrocellulose used may include ½ second, 15-30 second, 30-40 second, and/or 125/175 second to achieve a desired viscosity of the resulting nitrocellulose-based strip. In other embodiments, mixtures of different grades of nitrocellulose may be combined to create blends that achieve certain desired performance aspects, such as controlled pore sizes, and/or controlled liquid flow rates.

FIG. 1 shows a device and system wherein a strip of mixture 106 is cast directly onto the substrate 104 by the dispensing device 102. The substrate 104 may be a planar or non-planar solid structure, composed of solid material including, but not limited to, glass, metal, plastic, or other materials. In one embodiment, the dispensing device 102 may controllably distribute the polymer mixture 106 in a defined manner via spray coating, syringe extrusion, or slot dye coating. For example, dispensing device 102 may be a hypodermic and/or square-tip syringe needle. In another embodiment, the dispensing device 102 may comprise a multi-directional dispensing head 120 that may be moved/translated along a horizontal axis 152, lateral axis 156, and vertical axis 154. The dispensing head 120 and dispensing device 102 may in some examples be physically coupled to one another and as such may be moved together. However, in other examples, the dispensing head 120 and dispensing device 102 may not be physically coupled to one another, and as such the dispensing head 120 or dispensing device may be moved without movement of the other.

The dispensing head 120 may be any suitable device for dispensing the polymer mixture 106 such as a nozzle, injector, syringe pump, etc.

Axis system 150 includes the horizontal, lateral, and vertical axis, 152, 156, and 154, respectively. The lateral axis 156, horizontal axis 152, and vertical axis 154, may be orthogonal to one another, and as such may define a three dimensional coordinate system. Thus, the dispensing head 120 and dispensing device 102 may be movable in the planes defined by the axis system 150. As such, the dispensing device 102 may be movable within planes parallel to a first plane defined by the lateral axis 156 and horizontal axis 152. Further, the dispensing device 102 may be movable within planes parallel to a second plane defined by the horizontal axis 152 and vertical axis 154. The dispensing device 102 may further be movable along planes parallel to a third plane defined by the lateral axis 156 and vertical axis 154.

The dispensing device 102 may further include a pump (not shown in FIG. 1) that is compatible with the mixture 106, for pressurizing and delivering the mixture 106 to the dispensing head 120.

The dispensing device 102, and more specifically, the dispensing head 120, may be moved along any of the axis, 152, 154, and 156, by an actuator (e.g., electromechanical robotic arm), not shown in FIG. 1. Thus the actuator may adjust the position of the dispensing device 102 and dispensing head 120 above the substrate 104. The actuator may adjust the position of the dispensing device in response to signals received from a controller, the controller having computer readable instructions stored in non-transitory memory for controlling the dispensing device 102. Thus, in the description herein, any movement or change in position of the dispensing device 102 and/or dispensing head 120 may be achieved by the actuator in response to signals received from the controller, and/or inputs from a device operator.

For example, at step 1 of FIG. 1, the dispensing head 120 is positioned over the substrate 104. Specifically, the dispensing head 120 is positioned more proximate a first end 130 of the substrate 104 than a second end 140 of the substrate. The dispensing head 120 may be positioned a vertical distance above (e.g., in the positive direction along vertical axis 154) relative to the substrate 104. In some examples, the dispensing head 120 may be positioned a threshold vertical distance above surface of the substrate 104. Specifically, the dispensing head 120 may be positioned the threshold vertical distance above a top surface 124 of the substrate. The threshold vertical distance may be a distance in a range of distances between 0.2-5 mm. As shown in FIG. 1, the first end 130 may be parallel to the second end 140 of the substrate 104, where the ends 130 and 140 may be displaced relative to one another along the horizontal axis 152. Put more simply, the ends 130 and 140 may define the physical extent of substrate 104 along the horizontal axis 152. In this way, the second end 140 may be positioned to the right, or in the positive direction along the horizontal axis 152, relative to the first end 130.

Further, the substrate 104 may include a bottom face 122 opposite a top face 124. The bottom face 122 and top face 122 may define the extent of the substrate 104 along the vertical axis 154. As shown in FIG. 1, the bottom face 122 may be parallel to the top face 124 of the substrate 104, where the faces 122 and 124 may be displaced relative to one another along the vertical axis 154. Specifically the top face 124 may be vertically above the (e.g., displaced in the positive direction along the vertical axis 154) relative to the bottom face 122. Thus, the top face 124 may be orientated so that is faces the dispensing head 120, and the bottom face 122 may be orientated so that is faces away from the dispensing head 120.

The dispensing head 120 may be programmed to move along the horizontal axis 152, such that its motion defines the desired shape and size of the strip 107. Such motion allows the resulting wetted substrate area to be much larger than the viscosities and contact angles formed by the polymer mixture alone would naturally allow. Dispensing of the solution may be performed intermittently in a single pass or multiple passes, or continuously depending on a desired outcome.

Although the depicted embodiment in FIG. 1, is one dispensing device is shown with a single dispensing head to produce one individual strip, it should be appreciated that in other examples the dispensing device may comprise a multi-channel syringe-like dispensing head and one or more pumps to perform high accuracy, multi-channel dispensing. In one embodiment, the dispensing head comprises an array of flat hypodermic syringe needles. In this way, the system may increase its capacity and efficiency to produce a plurality of liquid polymer strips in one or more passes and runs of the system.

At steps 2 and 3, a mixture 106 is then ejected from the dispensing head 120 of the dispensing device 102 onto the substrate 104. The mixture 106 may be dispensed from the dispensing head 120 vertically downward, or in the negative direction along the vertical axis 154. Thus, the mixture 106 may travel in a substantially straight line, parallel to the vertical axis 154, in a downward direction (e.g., negative direction of vertical axis 154). Specifically the mixture 106 may be ejected onto the substrate beginning at a first position 132 of the substrate 104 to a second position 142 on the substrate 104. Thus, in steps 2 and 3, the dispensing head 120 may be moved along the horizontal axis 152 from vertically above the first position 132 to vertically above the second position 142. Dispensing of the mixture 106 may begin at the first position 132, continue as the dispensing head 120 is moved in the positive direction along the horizontal axis 152, and may then terminate when the dispensing head 120 reaches the second position 142. The first position 132, may be a location on the substrate 104 positioned a first distance 108 away from the first end 130 of the substrate 104. Further, the second position 142 may be a location on the substrate 104 positioned a second distance 110 away from the second end 140 of the substrate. In some examples, the first distance 108 and second distance 110 may be substantially the same. However, in other examples, the first distance 108 may be greater or smaller than the second distance 110. Thus, the first position 132 and second position 142 may define the physical extent of the dispensing region of the mixture 106 and may therefore define the length of the resulting nitrocellulose matrix.

The length of the nitrocellulose matrix may be adjusted by adjusting the first distance 108 and second distance 110. Thus, the dispensing of the mixture 106 may be configured to begin closer to or further away from the first end 130 of the substrate 104, and may be configured to end closer or further away from the second end 140 of the substrate, depending on a desired length of the nitrocellulose matrix, LFA device, and appropriate substrates.

In this way, the mixture 106 may begin dispensing onto the substrate 104 at the first position 132 via the dispensing head 120, when the dispensing head 120 is positioned vertically above the first position 132. The mixture 106 may continue to be dispensed as the dispensing head 120 is translated along towards the second end 140 of the substrate, away from the first end 130. In response to the dispensing head 120 reaching the second position 142, dispensing of the mixture 106 may be terminated.

At step 4 of FIG. 1, the polymer mixture 106 is allowed to dry to form a porous polymer strip 107. Thus, the porous polymer strip 107 may comprise the same compounds and elements as the mixture 107, but may be in solid physical state instead of a liquid state. Said another way, the strip 107 may be the same as the polymer mixture 106 except in a solid state instead of a liquid state. As such, the strip 107, may be referred to as solid nitrocellulose matrix strip 107 since the polymer mixture 106 comprises a nitrocellulose matrix. Therefore, the length of the polymer strip 107 may extend from the first position 132 to the second position 142 along the horizontal axis 152.

In yet another embodiment, a temperature control element, such as a water-cooled or heated plate (not shown), may be included to control the temperature of the substrate during the drying process. Lower or higher temperatures provided to the substrate may reduce or enhance the drying rate depending on desired conditions, and thus may serve to improve the porosity and uniformity of the strip 107 from piece-to-piece.

FIG. 2 shows an embodiment of the dispensing device 102 and substrate 104 shown above with reference to FIG. 1, with a framed mask 112 positioned on top of the substrate 104. Thus, the framed mask 112 may be positioned such that it is in one or more of face sharing, physical, and/or sealing contact with the top face 124 (shown above with reference to FIG. 1) of the substrate 104, and may be positioned between the substrate 104 and the dispensing device 102. Thus, the mask 112 may be physically coupled to the substrate 104, on the top face 124 of the substrate 104, where the top face 124 of the substrate 104 faces the dispensing device 102. The framed mask 112 may include a well 114 into which the mixture 106 is dispensed, for one or more of retaining, forming, and/or shaping the mixture 106 as it is dispensed from the dispensing device 102 and cools to form the strip 107. Thus, the steps shown above with reference to FIG. 1 for dispensing the mixture 106 may be same in FIG. 2, except that instead of the mixture 106 being dispensed directly onto the substrate 104, the mixture 106 may be dispensed onto the framed mask 112. Said another way, the mixture 106 may be dispensed into the well 114 in the same or similar manner to that described above with reference to FIG. 1 for dispensing the mixture 106 directly onto the substrate 104. As such, the well 114 may be sized such that it extends from the first position 130 to the second position 140. By including the framed mask 112 on the substrate 104, the shape, size, and other features of the strip 107 may be adjusted and/or controlled to a greater degree of accuracy. For example, the mask 112 may slow down the drying rate of the polymer mixture and thereby produce strips with increased uniformity. Furthermore, the thickness of the mask 112 and shape and size of well 114 may be varied to adjust the shape, thickness, and size of the wet polymer mixture strip. However, the thickness of the final polymer film may also depend on the nitrocellulose percent composition and relative porosity of the resulting strip.

In the embodiment shown in FIG. 2, the mask 112 is generally rectangular in shape and spans the majority of the substrate 104 along the horizontal axis 152 and lateral axis 156. In other embodiments, the shape and size of the mask 112 may be different than depicted in FIG. 2, and may comprise other various shapes and sizes. Specifically the mask 112 may be sized to approximately the same size as the top face 124 of the substrate 104. Moreover, the mask 112 may be made of silicone rubber or other appropriate materials. Use of materials such as silicone rubber ensures that an adequate seal is formed between the mask 112 and the substrate 104. In one example, the mask 112 is approximately 2-4 mm thick and spans generally across the substrate. In sum, the provision for the mask allows for defined deposition of polymer strips, manipulation of the final shape and placement of the polymer strip onto a substrate, and the option to deposit into non-planar three dimensional substrates.

The well 114 may be formed by a cut-out portion of the mask 112. In other examples, the well 114 may be included in the substrate 104, and may form a recess within the substrate 104. As such, the depth of the well 114 may be sized up to the thickness of the mask 112. As such, in some examples, the depth of the well may be in a range of depths, up to 4 mm. The well 114 may fully contain the mixture 106 as it is dispensed from the dispensing head 120. Thus, the well 114 may serve as a container, in which the mixture 106 may dry and form the strip 107. As such, the strip 107, may only by exposed on one surface. In some examples, all of the mixture 106 dispensed by the dispensing head 120 may be contained within the volume enclosed by the well 114, and substantially none of the mixture 106 may extend beyond the well 114. In this way, the shape of the strip 107 may conform to the shape/contour of the well 114. As such, the shape and/or size of the well 114 may be adjusted to produce a desired shape and/or size strip. In this way, the strip 107 may be approximately the same size and shape as the volume enclosed by the well 114. However, in other examples, the shape and/or size of the strip 107 may be different than that of the well 114.

The dispensing head 120 may be positioned over the well 114, and the mixture 106 may be dispensed into the well 114. In some examples, the dispensing head 120 may remain stationary while dispensing the mixture 106. However, in other examples, the dispensing head 120 may be moved along the horizontal axis 152 in the same or similar manner to that described above with reference to FIG. 1 when dispensing the mixture 106. For example, the dispensing head 120 may move from vertically above the first position 132, to vertically above the second position 142 while dispensing the mixture 106. The mixture 106 may accumulate in the volume enclosed by the well 114, as it is dispensed into the well 114. For example step 3, depicts how the volume of mixture 106 in the well 114 has increased relative to step 2, as more mixture 106 is added to the well 114 during dispensing. Dispensing of the mixture 106 may terminate when the dispensing head 120 reaches the second position 142. However, in other examples, the dispensing may terminate in response to a volume of the mixture 106 reaching a threshold volume within the well 114, and/or a liquid level in the well 114 reaching a threshold level. In some examples, the mixture 106 may be dispensed into the well 114 until substantially the entire volume enclosed by the well 114 is full of the mixture 106. However, in other examples, the dispensing the mixture 106 may stop when the mixture 106 occupies less than the entire volume enclosed by the well 114.

In this way, the liquid nitrocellulose mixture 106 may be dispensed by a dispensing device 102 onto a substrate 104 to form a solid nitrocellulose matrix strip 107. A dispensing head 120 of the device 102, may be moved over the substrate 104 while dispensing the mixture 106, to increase the uniformity of dispersal of the mixture 106 on the substrate 104. Further, a mask 114 including a well 114, may be positioned on top of the substrate 104, where the well 114 may be configured to receive and retain the mixture 106 dispensed by the dispensing head 120. Thus, the mixture may in some examples, be dispensed into the well 114. As such, a desired shape and/or size of the matrix strip 107 may be achieved by adjusting the shape and/or size of the well 114 to match the desired shape and/or size. In this way, after being dispensed and collected in the well 114, the mixture 106 may conform to the shape and/or size of the well 114. Thus, as the mixture 106 dries and solidifies to form the matrix strip 107, the matrix strip 107 may take on the shape and or size of the well 114.

FIG. 3 illustrates a chamber 300 into which the substrate 104 and mixture 106 may be placed for casting and drying of the mixture 106. The chamber 300 may include 6 walls which fully enclose an interior volume of the chamber 300 in which the substrate 104 is positioned. Thus, after dispensing the mixture 106 on the substrate 104, such as after step 3 shown above with reference to FIGS. 1 and 2, the substrate 104 including the mixture 106 may be placed within the chamber 300 for drying, solidifying and casting of the mixture 106.

However, in other examples, one or more of a nitrocellulose dispensing apparatus (e.g., dispensing device 102 shown in FIGS. 1 and 2) and the substrate 104 may be positioned and fully enclosed within the chamber 300, such that nitrocellulose mixture may be deposited onto the substrate 104 within the chamber 300. In this way, the nitrocellulose mixture may be exposed to the environment within the chamber 300 during deposition and subsequent drying. As such, the environment within the chamber 300 may be adjusted to regulate the drying rate of the mixture. Thus, the process of solidifying the mixture 106 into the strip 107 may occur in the chamber 300.

In some embodiments, the chamber 300 may comprise controls that regulate temperature, vapor content, humidity, etc. For example, the chamber 300 may include a heater 302 which may heat and accelerate the drying process of the mixture 106. In other examples, an air conditioner, dehumidifier and/or humidifier may be included in the chamber 300 for adjusting the temperature, humidity, etc., of the chamber 300. In this way, the rate at which the mixture 106 solidifies may be adjusted to a desired rate, where the desired rate may be determined based on a desired composition of the strip 107. Specifically, the desired rate may be determined based on a desired pore size and/or pore concentration of the strip 107. Thus, the rate at which the mixture 106 solidifies may be adjusted by adjusting one or more of the temperature and/or humidity of the chamber 300, to achieve the desired rate. In this way, one or more of a desired pore size, distribution, concentration, etc., may be achieved. For example, power supplied to the heater 302 may be increased to increase the drying rate of the mixture 106, and thus increase the density of pores formed during the drying of the mixture 106. As such, operation of the heater

302 may be adjusted to adjust the drying rate of the mixture 106, and therefore the pore size and/or distribution of pores in the strip 107.

In still further examples, one or more of the temperature and/or humidity in the chamber 300 may be differentially controlled across a length and/or width of the chamber 300. Said another way, the temperature and/or humidity in the chamber 300 may not be uniform in some example. Thus, the strip 107 may be exposed to a gradient of temperature and/or humidity, resulting in a gradient distribution of pore sizes within the film, depending on the position of the strip 107 in the chamber 300.

In yet further examples, a reservoir 304 may be included within the chamber 300. The reservoir 304 may include one or more of solvents such as water and/or acetone. A volume and/or composition of the reservoir 304 may be adjusted to adjust the vapor concentration in the chamber 300. In this way, by adjusting the vapor concentration in the chamber 300, the drying rate of the mixture 106 may be adjusted. As such, by adjusting one or more of the volume of the reservoir 304 and/or relative amount of different solvents included in the reservoir 304, the drying rate of the mixture 106 may be adjusted. In one example, a ratio of 1:4 acetone to water may be used in the reservoir 304. However, in other examples, the ratio may be greater or less than 1:4. Thus, by adjusting the relative amounts of different solvents in the reservoir 304, the drying rate of the mixture 106 may be adjusted to achieve the desired rate. As such, one or more of a desired pore size, distribution, and density may be achieved by adjusting the volume and/or composition of the reservoir 304. FIG. 4 shows an embodiment of the substrate 104 that a polymer mixture (e.g., mixture 106 shown above in FIGS. 1-3) may be dispensed directly upon. In one embodiment, the substrate 104 may be an elongated device housing comprising a top member 400 and bottom member 420, wherein members 400 and 420 can be snapped reversibly but securely together via engagement of complementary male and female parts: primary pins **408*a*-408*f* and holes 426*a*-426*f* on the top and bottom members 400 and 420, respectively. Specifically, the primary pins 408*a*-408*f* may be positioned on an interior facing first surface 402 of the top member 400. Thus, the pins 408*a*-408*f* may be physically coupled to the first surface 402, and may protrude from the first surface 402. The first surface 402 may be opposite an exterior facing second surface 403 of the top member 400. First surface 402** may be relatively flat and/or planar.

The holes **426*a*-426*f* may be positioned on an interior facing first surface 422 of the bottom member 420. First surface 422 may be relatively flat and planar. Thus, the holes 426*a*-426*f* may be physically coupled to the first surface 422, and may protrude from the first surface 422. Specifically, the holes 426*a*-426*f* may protrude from the first surface 422 and may each include an opening sized to receive the pins 408*a*-408*f*. Although six pins and six holes are shown in the example of FIG. 4, it is important to note that in other examples fewer or greater than six pins and/or holes may be used to physically couple the top member 400 and bottom member 420**.

As such, when coupling the top member 400 and bottom member 420 to one another, the top member 400 and bottom member 420 may be orientated so that the interior facing first surfaces, 402 and 422, respectively, are facing one another. Thus, the top member 400 may be flipped 180 degrees from the orientation shown in FIG. 4, so that the pins **408*a*-408*f* are pointed towards and/or facing the holes 426*a*-426*f*. More specifically, the top member 400 may be rotated around the central axis X-X' by approximately 180 degrees from the orientation shown in FIG. 4**.

In other words, each of the pins **408*a*-408*f* may fit into one of the respective holes 426*a*-426*f* formed along the perimeter of the interior facing surfaces 402 and 422 of the top and bottom members 400 and 420, respectively. In this way, the top member 400 and bottom member 420 may be physically coupled to one another, by inserting the pins 408*a*-408*f* into the holes 428*a*-428*f*. As such, when the pins 408*a*-408*f* are inserted into the holes 428*a*-428*f* and the top member 400 and bottom member 420 are physically coupled to one another, relative movement between the top member 400 and bottom member 420** may be restricted and/or inhibited.

A lip 404 may extend from first surface 402 of the top member 400, around a perimeter of the first surface 402. The lip 404 may be raised from the first surface 402. Similarly a lip 424 may be included on the first surface 422 of the bottom member 420 around a perimeter of the first surface 422. The lip 424 may be raised from the first surface 422.

When the top member 400 and bottom member 420 are coupled to one another, there may be constant and contiguous physical contact between the lips 404 and 424 of the top and bottom members, 400 and 420, respectively.

The top member 400 may include an exterior facing second surface 403, opposite the interior facing first surface 402. Similarly, the bottom member 400 may include an exterior facing second surface 423, opposite the interior facing first surface 422. Thus, when the top and bottom members 400 and 420, respectively, are physically coupled to one another to form the substrate 104, the interior facing first surfaces 402 and 422 may not be visible when viewing the substrate from exterior to the substrate 104. However, the exterior facing second surfaces 403 and 423 may be visible when the members 400 and 420 are physically coupled to one another. Second surfaces 403 may in some examples be relatively flat and/or planar surfaces.

In one embodiment, each of the top and bottom members 400 and 420, may be generally rectangular in shape and may be made from plastic or another appropriate material. The plastic of the substrate may be clear or opaque. The particular shape and construction of the top and bottom members 400 and 420, included in substrate 104, may be varied from the example illustrated, if desired.

Two examples of the bottom member 420 are shown in FIG. 4. In a first example, shown in FIG. 4 positioned above a second example, the mixture has not been dispensed onto the member 420. In the second example of the bottom member 420, shown in FIG. 4 below the first example, the mixture has been dispensed onto the bottom member 420 to form the nitrocellulose matrix strip 107. Thus, the first example shows the bottom member 420 prior to fabrication of the strip 107, such as in step 1 shown above with reference to FIGS. 1 and 2. The second example, shows the bottom member 420 after fabrication of the strip 107, where the mixture has been dispensed, polymerized, and dried to form the strip 107 on the bottom member 420.

In some examples, the bottom member 420 may include an area therein to receive the dispensed polymer mixture along the member's longitudinal axis. In one embodiment, a region 430 may be the area wherein the polymer mixture will be dispensed. Thus, region 430 may be the same or similar to well 114 described above with reference to FIG. 2, and as such, may be a recess within the first surface 422 of the bottom member 420 for receiving and retaining the mixture. As such, the region 430 may serve to one or more of shape, retain and/or form the strip 107. In other examples, the shape and size of region 430 may be an alternate configuration.

Once dried and polymerized under a set of specific conditions as previously described, the resulting strip 107 may include, but is not limited to: a collection region 431, a first and second detection region 432 and 434, respectively, and a handling region 436. In one example, collection region 431 may provide wicking action to facilitate capillary action of a fluid to detection regions 432 and 434. Moreover, the first detection region 432 may be a test region (denoted in this example as the letter "T") wherein one or more proteins of interest in an unknown sample fluid may bind to one or more pre-fixed and known binding ligands, such as a protein or antibody. In one example, the second detection region 434 (denoted in this example as the letter "C") may be a control region comprising one or more pre-fixed and known binding ligands considered to be present in a sample fluid. Thus, this region serves as a control to ensure the integrity of biomolecular structures in the sample, as well as functionality of the LFA test. The handling region 436 may be included on the strip 107 to enable a user to handle and maneuver the strip 107 without contaminating the detecting regions 432 and 434. The aforementioned descriptions of each region and configurations of a strip of polymer are one example, and may be modified, if desired.

Furthermore, the top member 400 may include one or more windows, such as windows 414 and 406. In one embodiment, window 416 may be an opening through which the polymer mixture and/or strip 107 may be observed after the mixture has been dispensed onto the bottom member 420 by a dispensing device (e.g., dispensing device 102 shown in FIGS. 1-2) and the top and bottom members 400 and 420, respectively are physically coupled together. Thus, the window 416 may be a hollow opening. The window 416 may be optically clear, so that light reflected from the strip 107, may pass in a relatively unobstructed manner through the window 416, and out of the substrate 104.

In one embodiment, the first surface 402 of the top member 400 and/or the first surface 422 of the bottom member 420 may include one or more secondary pins for retaining and holding the strip 107 in place. For example, as shown in FIG. 4, secondary pins **410*a*-410*c* may be physically coupled to the first surface 402 of the top member 400, such that the secondary pins 410*a*-410*c* extend inwards towards the bottom member 420. In some examples the secondary pins 410*a*-410*c* may be referred to as holding elements since they may serve to hold the strip 107 in place. Thus, the secondary pins 410*a*-410*c* may protrude from the first surface 402 and may physically contact edges of the strip 107, so that movement of the strip 107 relative to the bottom member 420 is restricted. Said another way, the holding elements 410*a*-410*c* may be positioned around a circumference of the strip 107. Additionally or alternatively, there may be pins on the first surface 422 of the bottom member 420 that restrict movement of the strip 107 relative to the bottom member 420**.

The top member 400 may also include a second collection window 414, including a funnel 412 so that the collection of a fluid of interest may be funneled through the window 414 to be absorbed by region 431 of a strip 107. Thus, after the strip 107 has been formed, and the top and bottom members 400 and 420 have been physically coupled to one another, a fluid of interest may be poured/dispensed onto the region 431 via the window 414. Thus, the fluid of interest may first enter the substrate 104 via the window 414 of the top member 400. As such, the window 414 may be positioned directly vertically above the region 431, so that fluid entering the substrate 104 via the window 414, collects in the region 431.

Adjacent to the first window 416 may be denotations of one or more detection regions, such as test region 432 and control region 434. For example, in one embodiment, a letter "C" may be printed on the surface of top member 400 directly vertically above control region 434 if viewed through the opening to the strip underneath the top member 400. Similarly, in another example, a letter "T" may be printed in a similar fashion directly above the test region 432. Thus, the letters may be printed onto the first window 416, to indicate which portion of the strip 107 is being viewed underneath the top member 400. Any combination of symbols may be printed on either member to denote various features. Thus, the window 416 may allow a user to view the test region 432 and control region 434 from exterior the substrate after the fluid of interest has been dispensed on the strip 107.

FIG. 5 shows a side view embodiment of a nitrocellulose matrix strip 500. Thus, matrix strip 500 may be the same or similar to strip 107 described above with reference to FIGS. 1-4. Strip 500 is generally a flat, elongated and rectangular piece comprising three regions 504, 508 and 512, and is disposed directly on the housing substrate 502. Housing substrate 502 may be same or similar to substrate 104 described above with reference to FIGS. 1-4. Each of these regions 504, 508, and 512 may be formed by the system and methods disclosed herein, and comprises a polymer mixture including nitrocellulose.

First region 504 may be an area wherein a sample is loaded and received. Thus first region 504 may be same or similar to region 431 described above with reference to FIG. 4. More specifically, a collection window configured to direct a fluid of interest to the region 504 (e.g., window 414 shown in FIG. 4) may be disposed directly above region 504. In one embodiment, region 504 may be provided with a fibrous layer 506 deposited over the nitrocellulose matrix strip 500 that facilitates wicking and capillary action to distribute sample fluid to the downstream regions 508 and 512. Specifically, the layer 506 may be disposed on a top surface 522 of region 504, the top surface 522 opposite a bottom surface 524, where the bottom surface 524 may be in physical contract with the substrate 502 and/or mask 520. Thus, the top surface 522 may face away from the substrate 502, and the region 504 may be positioned between the substrate 502 and the layer 506.

Adjacent to and downstream of region 504 is a first partition 516, wherein approximately no ligands, proteins, antibodies or other biomolecules may be loaded and impregnated into strip 500. Thus, substantially no binding and/or detection may occur between the sample and the impregnated binding biomolecules in first partition 516. The first partition 516 may be sized to approximately the same width as ligand region 508. Said another way, first partition 516, may be raised from the surface of the substrate 502 by an amount approximately equal to that of the ligand region 508.

Adjacent to first partition 516 on the opposite side from region 504 is a first ligand region 508. In one example, ligand region 508 may the same or similar to test region 432 discussed previously in FIG. 4, wherein one or more known binding partners or ligands of a desired biomolecule of interest, such as a protein or antibody, are impregnated into the strip 500. In one example, to form this region, a solution containing a plurality of binding ligands are dispensed and loaded onto first ligand region 508. Through capillary action, the loaded binding ligands disperse within the nitrocellulose matrix and are stably fixed and integrated within the matrix. After fixation of ligands to ligand region 508 of the strip, a blocking solution may be applied to the strip 500. The blocking solution may reduce and/or prevent immobilization of biomolecules such as proteins or antibodies. As such, after application of the blocking solution to the strip 500, proteins within the sample fluid may only traverse the nitrocellulose strip 500 by capillary flow during. Blocking solutions may include but are not limited to one or more of protein blocking solutions and/or non-protein polymer blocking solutions. Therefore, interaction, binding or cross-linking of one or more biomolecules in the unknown sample to the fixed ligands in the strip 500 may occur as the sample fluid moves through region 508 from collection region 504 and first partition 516. Thus, the sample fluid may disperse across the strip 500 from left to right in FIG. 5 as shown by flow arrow 520.

In another example, first ligand region 508, may include a chromogenic substrate, which may recognize and enzymatically react to the biomolecule of interest in the sample, or crosslinking or binding of the biomolecule of interest and the integrated ligand, to produce a visible color. The chromogenic substrate may be applied to nitrocellulose strip 500 at region 508 by mixing it with the solution of the binding ligands, or may be dispensed separately in another step. The visible color of the chromogenic substrate may be viewed through a detection window (e.g., window 416 shown in FIG. 4) to determine whether a biomolecule of interest is present in the unknown sample.

Downstream and adjacent to the ligand region 508 is a non-overlapping second partition 518. In some examples, the size and length of second partition 518 may be comparable to first partition 516. In other examples, second partition 518 may be larger and longer than first partition 516. Thus, the first partition 516, ligand region 508, and second partition 518 may be approximately flush with one another. Adjacent to and sequentially downstream of second partition 518 is a second ligand region 512. The second ligand region 512 may the same or similar to control region 434 described above with reference to FIG. 4. As described in FIG. 4, in one example, the second detection region 512 may be a control region comprising one or more known binding partners or ligands to a protein that is generally considered to be present in a sample fluid. In one embodiment, the ligands loaded into region 508 may be substantially dissimilar to the ligands loaded into region 512 in structure and/or function. Thus, region 508 may serve as a control to ensure the integrity of biomolecular structures in the sample and strip 500, as well as the functionality of the LFA test. Similar to the first ligand region 508, a chromogenic substrate may also be included in the second ligand region 512. In some embodiments, the chromogenic substrate may be the same or different than the substrate used in the first ligand region 508. The visible color of the chromogenic substrate may be viewed through the detection window to determine if the biomolecule of interest is present in the unknown sample.

An additional handling region may be included at either end of the strip, wherein a user can handle and maneuver the nitrocellulose strip without contaminating sensitive wicking and detection regions (not shown).

In addition, FIG. 5 shows an example of a nitrocellulose strip 550 including a based piece 520 disposed between the substrate 502, and the strip 550. In one embodiment, strip 550 is identical to strip 500. Thus components of the strip 550 may be the same or similar to strip 500. As such components of strip 550 numbered the same as components of strip 500 already described herein, may not be reintroduced or described again. In the example of strip 550, the strip 500 may be dispensed onto the base piece 520, which may be disposed on the substrate 502. Thus, the strip 500 may not be disposed directly on the substrate 502. Base piece may be the same or similar to mask 112 described above with reference to FIG. 2. Thus, base piece 520 may be disposed directly atop housing substrate 502. In one example, piece 520 is formed from a polymer mixture and dispensed by a dispensing device (e.g., dispensing device 102 shown in FIG. 102) onto substrate 502. After polymerization and drying, strip 550 may be dispensed and formed onto the base piece 520. In this way, base piece 520 may provide increased support for the nitrocellulose strip 550 as compared to examples, where the base piece 520 is not included, such as in the example shown for strip 500.

In some examples, the locations of the various detection regions on the strips 500 and 550 may vary. For example, ligand regions 508 and 512 may be switched such that the control region is upstream of the test region. In yet other embodiments, various detection regions may fully or partially overlap each other or may comprise separate, non-overlapping regions (such as those shown in FIG. 5). Similarly, the sample collection region 504 may overlap the regions impregnated with the detection ligands or may be a separate region. It may be appreciated that the specific locations of the various regions on strips 500 and 550 may vary depending on desired outcomes.

FIG. 6 indicates an example method 600 for forming a polymeric nitrocellulose matrix strip (e.g., strip 107 shown in FIGS. 1-4), wherein a defined area of porous nitrocellulose is deposited onto a substrate (e.g., substrate 104 shown in FIGS. 1-4) by a dispensing device (e.g., dispensing device 102 shown in FIGS. 1-2). In some examples a controller with non-transitory memory may include computer readable instructions for executing the method 600. As such, in some examples, the method 600 may be performed by the controller.

Method 600 begins at 602, which comprises combining and mixing components comprising a polymer mixture (e.g., mixture 106 shown in FIGS. 1-3) where the components may include one or more of a solvent, metasolvent, non-solvent, and/or nitrocellulose. The components of the polymer mixture may further contain, but may not be limited to various grades and types of plasticizers and detergents. The method at 602 may further comprise determining desired amounts, volumes, types, and/or grades of the components to be mixed at 602. Thus, the desired amount/volume and type/grade of each of the components mixed at 602 may be determined and combined with one another to form the mixture.

After combining and mixing the components of the mixture at 602, method 600 may continue to 604 which may comprise loading the mixture into a dispensing device (e.g., dispensing device 102 shown in FIGS. 1-2). As described above with reference to FIGS. 1 and 2, the position of the dispensing device may be adjusted in three dimensional space.

In some examples, method 600 may continue from 604 to optional step 606, which comprises fixing a mask (e.g., mask 112 shown in FIG. 2) onto the substrate. In some examples, an adhesive may be applied between the mask and the substrate. However, in other examples, other coupling techniques such as fasteners and thermal bonding may be used to adhere the mask to the substrate. In other examples, method 600 may proceed directly to 608 from 604, without fixing the mask onto the substrate at 604. Thus, in some examples, the mask may not be included on the substrate.

Method 600 may then proceed from either 604 or 606 to 608 which comprises positioning the dispensing device over the substrate at a desired starting location (e.g., first location 132 shown in FIGS. 1 and 2. In some examples, the method 600 may comprise positioning the dispensing device over a well (e.g., well 114 shown in FIG. 2) included in the mask. The desired starting location may be approximately between 0.2 mm to 5 mm from the surface of substrate.

Once the dispensing device is positioned over the desired location of the substrate, the method 600 may continue to 610 which comprises depositing the polymer mixture onto the substrate. Dispensing the mixture may include supplying current to an electromechanical injector or valve in the dispensing device to dispense the mixture onto the substrate. In examples where method 600 perform 606 and the mask is included, dispensing the mixture may comprise dispensing the mixture onto the mask, and specifically into the well included in the mask. Further method 600 at 610 may include moving the dispensing device across the longitudinal axis of the substrate. Thus, the controller may send signals to an actuator of the dispensing device, to move the dispensing device in a substantially straight line from the desired starting location across the longitudinal axis of the substrate, desired end location (e.g., second location 142 shown in FIGS. 1 and 2), where the desired end location may be horizontally displaced from the starting location. Further, the vertical positioning of the dispensing device may be maintained. Said another way, the distance between the dispensing head and the substrate may be maintained while moving the dispensing head from the starting location to the end location.

In response to the dispensing head reaching the end location method 600 may continue from 610 to 614 which comprises terminating the dispensing of the mixture and withdrawing the dispensing device from the substrate. Thus, an injector or valve of the dispensing device may be closed at 614, so that the mixture ceases to flow out of the dispensing device. Withdrawing the dispensing device may comprise moving the dispensing device so that the vertical distance between the dispensing device and the substrate is increased.

Method 600 may then continue from 614 to 616, which comprising drying the mixture on the substrate. Thus, the method 600 at 616 may comprise solidifying the mixture, or said another way, changing the phase of the mixture from liquid to solid. In some examples, the mixture may be placed in a sealed chamber (e.g., chamber 300 shown in FIG. 3) to increase or decrease the rate at which the mixture dries and/or solidifies. As discussed above, the formation of pores as the polymer film dries may be dependent on the differential evaporation rates of the solvent, meta-solvent, and non-solvent. Therefore, control over the evaporation conditions may be adjusted at 616 to regulate the pore formation and the performance characteristics of the films.

To control the evaporation rates of the films, various incubation parameters, such as temperature, local vapor concentration above the mixture, and presence of framed mask, may be controlled. For instance, in a condition in which a certain vapor pressure is desired and when using a system comprising the combination of acetone, ethanol, and water, an incubation chamber (such as chamber 300 of FIG. 3) with a reservoir of approximately 20% acetone and 80% water may be provided during the drying process. These conditions may result in the local environment above the polymer mixture containing a specific fraction of acetone vapor that results in large and uniform pore sizes in the nitrocellulose strip. Alternatively, the relative humidity in the chamber can be manipulated to provide an environment that causes controlled evaporation of solvent and precipitation and/or solidification of polymer from solution.

In addition, a temperature at the substrate may affect the evaporation rate, so that modulation of temperature at 616 during drying of the polymer mixture may result in desirable outcomes. For example, again using the acetone, ethanol, and water solvent system described above, casting at 55° F. (e.g., 12-13° C.) may provide strips (e.g., strip 107 shown in FIGS. 1-4) with an appropriate fluid flow rate and larger pore sizes. Depending on the solvent systems used and the relative differential evaporation rates of solvent, meta-solvent, and non-solvent, casting at increased temperatures can result in films with smaller pores, resulting in slower liquid capillary motion. The drying temperature of a substrate can be manipulated by controlling the temperature of the substrate bed. Therefore, by introducing a temperature gradient across the substrate bed, differential relative evaporation rates of solvent from a film strip can be induced, resulting in different pore sizes in different areas of a single strip. Varying and optimizing the temperature across the deposited area during method 600 may also comprise one aspect of step 616.

In this way, one or more of the vapor concentration, temperature, etc., may be adjusted at 616 to increase or decrease a size of pores formed during drying and solidifying of the mixture. By regulating the formation and/or size of pores in the mixture as it dries to from the strip, different concentrations and/or sizes of pores may be formed in different areas of the strip, which can result in different differential flow rates within the strip. In this way, flow rates across the strip may be adjusted by controlling the location, concentration, and/or size of the pores, where formation and/or size of the pores may be adjusted by increasing and/or decreasing one or more of the temperature and/or vapor concentration of the environment where the mixture is dried at 616. Specifically by increasing the temperature, the evaporation rate of the solvent may be increased, resulting in reduced solubility of the non-solvent, which may lead to the formation of emulsified non-solvent droplets, and thus increased pore density. In further examples, decreasing the humidity may increase the evaporation rate of the solvent, thereby increasing pore density. Thus, the drying and polymerizing at 616 may comprise one or more of increasing the temperature and/or reducing the humidity to increase pore density.

Therefore, one or more of solvent/non-solvent composition and relative concentrations, nitrocellulose composition and concentration, additive composition and concentration, and environmental conditions including temperature, humidity, vapor pressure, air flow, may be adjusted to adjust one or more of pore size, density, and distribution. By adjusting the pore size, density and/or distribution, flow characteristics of the strip may be adjusted.

Specifically, the method 600 at 616 may include increasing the temperature in response to one or more of an increase in a desired pore density, and/or a decrease in desired pore size. Additionally or alternatively, the method 600 at 616 may include decreasing the temperature in response to one or more of a decrease in the desired pore density and/or an increase in the desired pore size. The temperature may be increased by increasing power supplied to a heater (e.g., heater 302 shown in FIG. 2). Conversely, the temperature may be decreased by decreasing power supplied to the heater.

Additionally or alternatively, the method 600 at 616 may include decreasing the humidity in response to one or more of an increase in the desired pore density and/or a decrease in the desired pore size. Further, the method 600 at 616 may include increasing the humidity in response to one or more of a decrease in the desired pore density and/or an increase in the desired pore size.

More simply, the drying rate of the mixture may be adjusted by adjusting one or more of the ambient temperature and/or humidity of the chamber in which the mixture dries. As such, one or more of the size, distribution, and density of the pores may be adjusted by adjusting one or more of the ambient temperature and/or humidity of the chamber.

From the above description, it can be understood that the system and method disclosed for production of lateral flow assays have several advantages, namely the reduction of process and assembly steps resulting in increased efficiency, reduced production costs, and increased value of final product. Specifically, by forming a nitrocellulose matrix strip on a substrate, processes such as cutting of the strip may be eliminated. Thus, by dispensing a liquid mixture of the nitrocellulose matrix into a well formed on the substrate, the shape of the resulting strip may be configured to any desired shape by adjusting the shape of the well. In this way, the constancy and repeatability of producing such strips may be increased.

Further by regulating the temperature and/or humidity during drying and/or solidifying the liquid mixture into the strip, a temperature and/or humidity to which the mixture is exposed may be adjusted to provide a desired pore size, shape, and composition for application in lateral flow assay devices. Pore sizes in the strip may affect one or more performance characteristics such as protein binding capacity, speed of fluid transfer, and detection sensitivity. For example, larger pore sizes may allow faster fluid transfer which may reduce procedural time. However, larger pores may also decrease protein binding capacity of capture ligands, lowering the detection sensitivity. Therefore, a desired pore size maybe determined based on the desired performance characteristic of the assay being produced. Further, various features may enable ease of development and production, eliminating time-consuming steps of cutting and fitting seen in current systems to manufacture porous film strips.

It is further understood that the lateral flow test device and method described and illustrated herein represents only example embodiments. It is appreciated by those skilled in the art that various changes and additions can be made to such device and method without departing from the spirit and scope of this application. For example, method 600 may comprise additional steps for optimizing pore size utilizing various dispensing head types, robotic set-ups and selected combinations of solvents, non-solvents, nitrocellulose, hydrophilic additives, detergents and meta-solvents. Moreover, materials aside from nitrocellulose may be used, such as polyamide-based membranes, glass fiber, cellulose and other microporous polymers, singularly or in combination with other polymers, depending on compatibility with a variety of ligands and/or binding structures, such as biomolecules (e.g., proteins, antibodies, capture ligands) and nanoparticles (e.g., gold).

The invention claimed is:

1. A method for forming a polymeric strip, comprising:

positioning a dispensing device a threshold vertical distance above a substrate;

dispensing a liquid polymer mixture from the dispensing device onto a planar surface of the substrate, and while dispensing the polymer mixture, moving the dispensing device from a first position to a second position, wherein the first position corresponds to a beginning of the polymeric strip and the second position corresponds to an end of the polymeric strip;

terminating the dispensing in response to the dispensing device reaching the second position; and drying the mixture.

2. The method of claim 1, wherein the moving the dispensing device comprises translating the dispensing device in a plane parallel to the planar surface of the substrate such that the threshold vertical distance is maintained during the moving, wherein the dispensing device comprises a housing with an upper first portion and a lower second portion, the lower second portion including the planar surface, and further comprising a nitrocellulose matrix strip disposed on the planar surface, the strip including one or more ligand regions.

3. The method of claim 1, wherein the first position is a position more proximate a first end of the planar surface than a second end of the planar surface, where the second position is a position more proximate the second end than the first end of the planar surface, and wherein the planar surface includes a plurality of holding elements.

4. The method of claim 1, further comprising, withdrawing a dispensing head of the dispensing device from the planar surface in response to terminating the dispensing, the withdrawing comprising increasing a vertical distance between the dispensing head and the planar surface.

5. The method of claim 1, wherein the drying comprises one or more of heating, cooling, humidifying, and dehumidifying a sealed chamber to a desired humidity and temperature, the desired humidity and temperature determined based on a desired drying rate, the desired drying rate determined based on one or more of a desired pore size, distribution and density, and incubating the mixture in the sealed chamber with a reservoir of volatile solvent, either in pure form or in a mixture with another solvent.

6. A method for producing a nitrocellulose strip using a dispensing device, comprising:

dispensing a nitrocellulose-based polymer mixture onto a planar surface of a substrate, spreading the polymer mixture with a head of the dispensing device, moving the dispensing device from a first position to a second position, wherein the first position corresponds to a beginning of the nitrocellulose strip and the second position corresponds to an end of the nitrocellulose strip, and terminating the dispensing in response to the dispensing device reaching the second position.

7. The method of claim 6, wherein the first position is a position more proximate a first end of the planar surface than a second end of the planar surface, and further comprising withdrawing the dispensing device head from the planar surface in response to terminating the dispensing.

8. The method of claim 6, further comprising drying the polymer mixture, wherein the drying comprises one or more of heating, cooling, humidifying, and dehumidifying a sealed chamber to a desired humidity and temperature.

9. The method of claim 8, further comprising incubating the polymer mixture in the sealed chamber with a reservoir of volatile solvent, either in pure form or in a mixture with another solvent.

* * * * *